United States Patent
Sachidanadam

(10) Patent No.: US 12,251,519 B2
(45) Date of Patent: Mar. 18, 2025

(54) PORTABLE OXYGEN GENERATOR SYSTEM

(71) Applicant: O2-Matic Products Private Limited, Bangalore (IN)

(72) Inventor: John Paul Thambusami Joy Sachidanadam, Bangalore (IN)

(73) Assignee: O2-Matic Products Private Limited (IN)

(*) Notice: Subject to any disclaimer, the term of this patent is extended or adjusted under 35 U.S.C. 154(b) by 960 days.

(21) Appl. No.: 17/306,997

(22) Filed: May 4, 2021

(65) Prior Publication Data

US 2021/0402128 A1    Dec. 30, 2021

(30) Foreign Application Priority Data

Jun. 24, 2020   (IN) .............................. 202041026785

(51) Int. Cl.
*A61M 16/10*   (2006.01)
*A61M 16/16*   (2006.01)
(Continued)

(52) U.S. Cl.
CPC ........ *A61M 16/1005* (2014.02); *A61M 16/16* (2013.01); *A62B 7/08* (2013.01);
(Continued)

(58) Field of Classification Search
CPC .......... A61M 16/1005; A61M 16/0063; A61M 16/105; A61M 16/101;
(Continued)

(56) References Cited

U.S. PATENT DOCUMENTS 6,446,630 B1 * 9/2002 Todd, Jr. ........... A61M 16/0051
                                                    128/205.24
8,123,497 B2  2/2012 Richey, II et al.
(Continued)

FOREIGN PATENT DOCUMENTS

EP    1890074 A1    2/2008
EP    3416713 A1    12/2018

OTHER PUBLICATIONS

Medura Oxygen Concentrator; https://www.mygetwellstore.com/medura-oxygen-concentrator.html#/tab-product1.

*Primary Examiner* — Kendra D Carter
*Assistant Examiner* — Maap Ellabib
(74) *Attorney, Agent, or Firm* — Jason C. Cameron

(57) ABSTRACT

A cartridge system comprising a container and at least four cartridges for generating oxygen, a compressor for compressing the generated oxygen, at least one storage tank configured to store the compressed oxygen received from the compressor, an oxygen pressure regulator enabling a uniform flow of oxygen at pre-defined oxygen pressure, an oxygen flow control knob regulating flow ratio of the oxygen being supplied to the patient in an instant, a humidifier means imparting humidity to the oxygen being supplied to a patient, and a display unit displaying a set of information associated with the system and communicatively coupled to the portable oxygen generator system 10 via wireless network. The cartridges may be triggered in a plurality of ways to maintain a continuous outflow of generated oxygen for a longer duration. Further, the operation of the system may be monitored or controlled wirelessly from a distant location.

17 Claims, 8 Drawing Sheets

(51) Int. Cl.
*A62B 7/08* (2006.01)
*A62B 9/00* (2006.01)
*A62B 9/02* (2006.01)
*A62B 9/04* (2006.01)

(52) U.S. Cl.
CPC ............... *A62B 9/00* (2013.01); *A62B 9/003* (2013.01); *A62B 9/02* (2013.01); *A62B 9/04* (2013.01); *A61M 2205/3331* (2013.01); *A61M 2205/3334* (2013.01); *A61M 2205/3584* (2013.01)

(58) Field of Classification Search
CPC ...... A61M 16/16–168; A61M 16/1075; A61M 16/1095; A61M 16/1045; A61M 2209/084; A62B 9/02; A62B 9/00; A62B 9/04; B01D 2253/116; B01D 53/047; B01D 2259/4566
See application file for complete search history.

(56) References Cited

U.S. PATENT DOCUMENTS

| | | | |
|---|---|---|---|
| 8,677,998 | B2 | 3/2014 | Yamaura et al. |
| 2007/0137487 | A1* | 6/2007 | Whitley ............. B01D 53/0415 96/121 |
| 2012/0289765 | A1* | 11/2012 | Kaushansky ....... A61M 60/495 600/18 |

* cited by examiner

PORTABLE OXYGEN GENERATOR SYSTEM

EARLIEST PRIORITY DATE

This application claims priority from a provisional patent application filed in India having Patent Application No. 202041026785, filed on Jun. 24, 2020, and titled "A PORTABLE OXYGEN GENERATOR SYSTEM".

FIELD OF INVENTION

Embodiments of a present invention relate to an oxygen generator, and more particularly to a portable oxygen generator system.

BACKGROUND

In certain situation, oxygen is stored in tanks and provided to people having certain breathing issues or undergoing operation so as to maintain a desired level of oxygen in breathing air. In certain other cases, tanks storing oxygen under pre-defined pressure referred to as oxygen cylinders is also used by people in other situations such as travel in hospitals, ambulance, space shuttle, scuba diving, mountaineering and the like for maintaining required supply of oxygen. However, such oxygen cylinders are usually composed of metals and are heavy in weight and big in size which creates a problem for transportation or porting of such cylinders. Bulky oxygen cylinders make it very difficult to carry them around. Also, refilling of oxygen into the cylinder is a lengthy and expensive process. Thereby oxygen generators are being used to enable easy porting of the oxygen.

In one such approach, an oxygen generator is used to generate and store the oxygen upon combining a number of chemicals together in a vessel at a required pressure. Consequently, the oxygen generator generates the oxygen at any instant of time. However, rate of flow of generation of oxygen by the oxygen generator cannot be maintained and also duration for which the oxygen generator can generate oxygen is limited or short. Such limitation may not produce a required quantity of oxygen for a desired duration of time. Also, a user needs to manually mix number of chemicals in order to generate the oxygen. Such human interventions can lead to inaccuracy in ratio of the number of chemicals, thereby making the oxygen generator less efficient and less accurate. Also, the transportation of the oxygen generator is a real challenge is such approaches. Due to the bulk of the oxygen generator, transporting it from one location to another becomes difficult and requires more of manpower. This makes the presently known solutions less effective in emergency medical situations.

Hence, there is a need for an improved portable oxygen generator system to address the aforementioned issues.

BRIEF DESCRIPTION

In accordance with one embodiment of the disclosure, a portable oxygen generator system is provided. The portable oxygen generator system includes a cartridge system. The cartridge system includes a container having a generator drawer operable in a lateral direction. The generator drawer includes at least four hollow chambers. The at least four hollow chambers are separated by a pre-defined structure. The cartridge system also includes at least four cartridges housed within the corresponding at least four hollow chambers. Each of the at least four cartridges is configured to generate oxygen upon reaction of a pre-defined amount of water with one or more chemicals in a chemical chamber located within the at least four cartridges. The cartridge system also includes an accumulator operatively coupled to the at least four cartridges via a set of pipes and configured to receive and accumulate the generated oxygen. The portable oxygen generator system also includes a compressor operatively coupled to the accumulator. The compressor is configured to receive accumulated oxygen from the accumulator and compress received oxygen thereby reduces volume required to store the compressed oxygen. The portable oxygen generator system also includes at least one storage tank operatively coupled to the compressor. The at least one storage tank is configured to store the compressed oxygen received from the compressor. The portable oxygen generator system also includes an oxygen pressure regulator operatively coupled to the at least one storage tank. The oxygen pressure regulator is configured to enable a uniform flow of oxygen at pre-defined oxygen pressured required for breathing at an output coupled to a patient to supply the oxygen upon being humidified. The portable oxygen generator system also includes an oxygen flow control knob operatively coupled to the oxygen pressure regulator and the at least one storage tank. The oxygen flow control knob is configured to regulate flow ratio of the oxygen being supplied to the patient in an instant. The portable oxygen generator system also includes a humidifier means operatively coupled to the at least one storage tank. The humidifier means is configured to impart humidity to the oxygen being released from the at least one storage tank to the output coupled to the patient to supply the oxygen. The portable oxygen generator system also includes a pneumatic circuitry means sealed to the cartridge system. The pneumatic circuitry means incudes an electronic control circuit configured to control an operation of the compressor. The humidifier is housed on one of a corner of the pneumatic circuitry means. The oxygen flow control knob is attached to a body of the pneumatic circuitry means. The portable oxygen generator system also includes a wheelbase attached to a bottom surface of one of or the pneumatic circuitry means the generator drawer to impart mobility of the portable oxygen generator system. The portable oxygen generator system is configured to facilitate unidirectional flow of oxygen generated in the at least four cartridges via a plurality of valves to the humidifier means.

To further clarify the advantages and features of the present disclosure, a more particular description of the disclosure will follow by reference to specific embodiments thereof, which are illustrated in the appended figures. It is to be appreciated that these figures depict only typical embodiments of the disclosure and are therefore not to be considered limiting in scope. The disclosure will be described and explained with additional specificity and detail with the appended figures.

BRIEF DESCRIPTION OF THE DRAWINGS

The disclosure will be described and explained with additional specificity and detail with the accompanying figures in which.

Further, those skilled in the art will appreciate that elements in the figures are illustrated for simplicity and may not have necessarily been drawn to scale. Furthermore, in terms of the construction of the device, one or more components of the device may have been represented in the figures by conventional symbols, and the figures may show only those specific details that are pertinent to understanding the embodiments of the present disclosure so as not to obscure the figures with details that will be readily apparent to those skilled in the art having the benefit of the description herein.

DETAILED DESCRIPTION

For the purpose of promoting an understanding of the principles of the disclosure, reference will now be made to the embodiment illustrated in the figures and specific language will be used to describe them. It will nevertheless be understood that no limitation of the scope of the disclosure is thereby intended. Such alterations and further modifications in the illustrated system, and such further applications of the principles of the disclosure as would normally occur to those skilled in the art are to be construed as being within the scope of the present disclosure.

The terms "comprises", "comprising", or any other variations thereof, are intended to cover a non-exclusive inclusion, such that a process or method that comprises a list of steps does not include only those steps but may include other steps not expressly listed or inherent to such a process or method. Similarly, one or more devices or sub-systems or elements or structures or components preceded by "comprises . . . a" does not, without more constraints, preclude the existence of other devices, sub-systems, elements, structures, components, additional devices, additional sub-systems, additional elements, additional structures or additional components. Appearances of the phrase "in an embodiment", "in another embodiment" and similar language throughout this specification may, but not necessarily do, all refer to the same embodiment.

Unless otherwise defined, all technical and scientific terms used herein have the same meaning as commonly understood by those skilled in the art to which this disclosure belongs. The system, methods, and examples provided herein are only illustrative and not intended to be limiting.

In the following specification and the claims, reference will be made to a number of terms, which shall be defined to have the following meanings. The singular forms "a", "an", and "the" include plural references unless the context clearly dictates otherwise.

Embodiments of the present disclosure relate to a portable oxygen generator system. As used herein, the term "oxygen generator" is defined as a medical device that generates oxygen as a result of a reaction of one or more elements.

Figure 1:
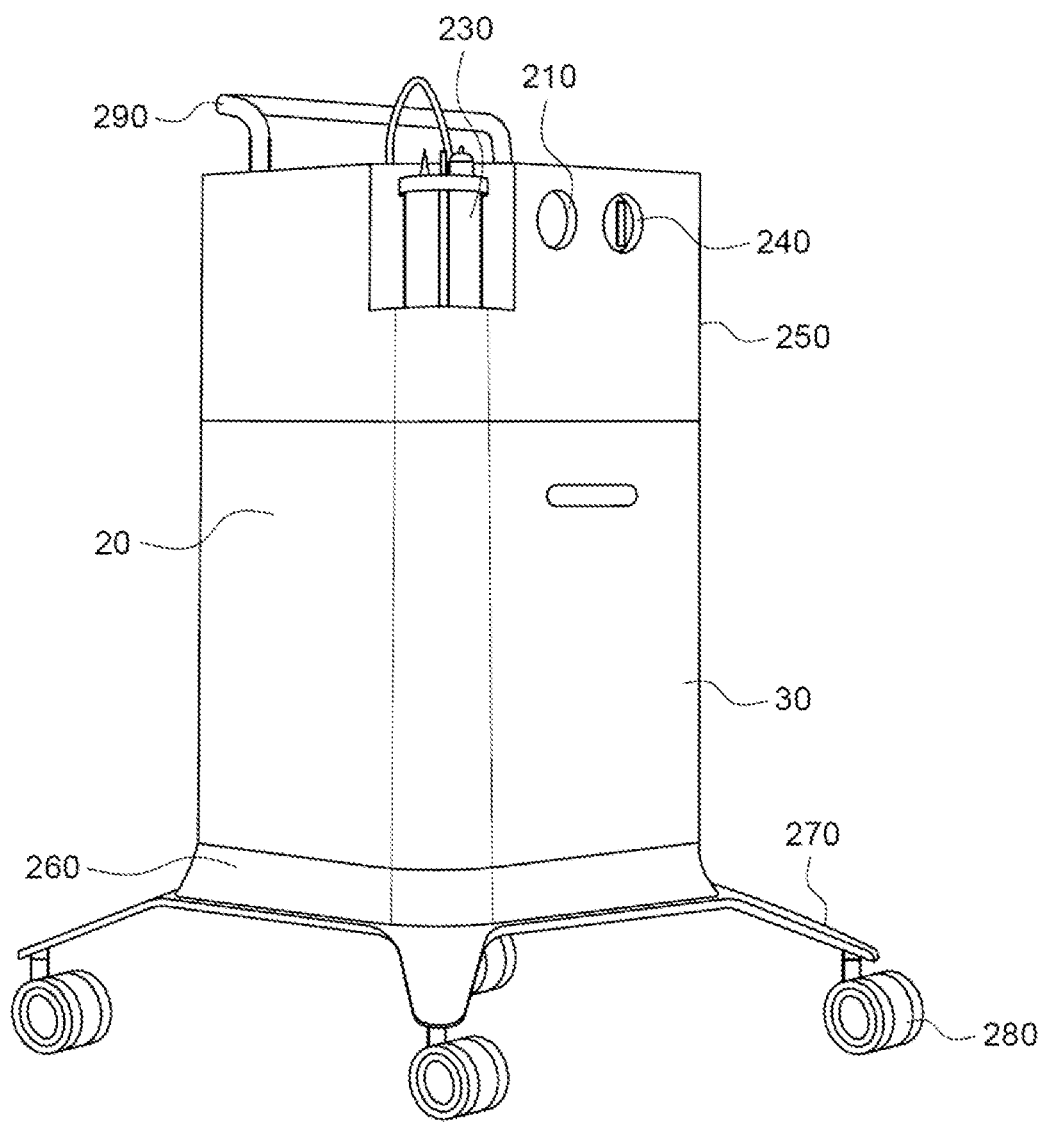
FIG. 1 is a schematic representation of a portable oxygen generator system in accordance with an embodiment of the present disclosure.
Figure 2:
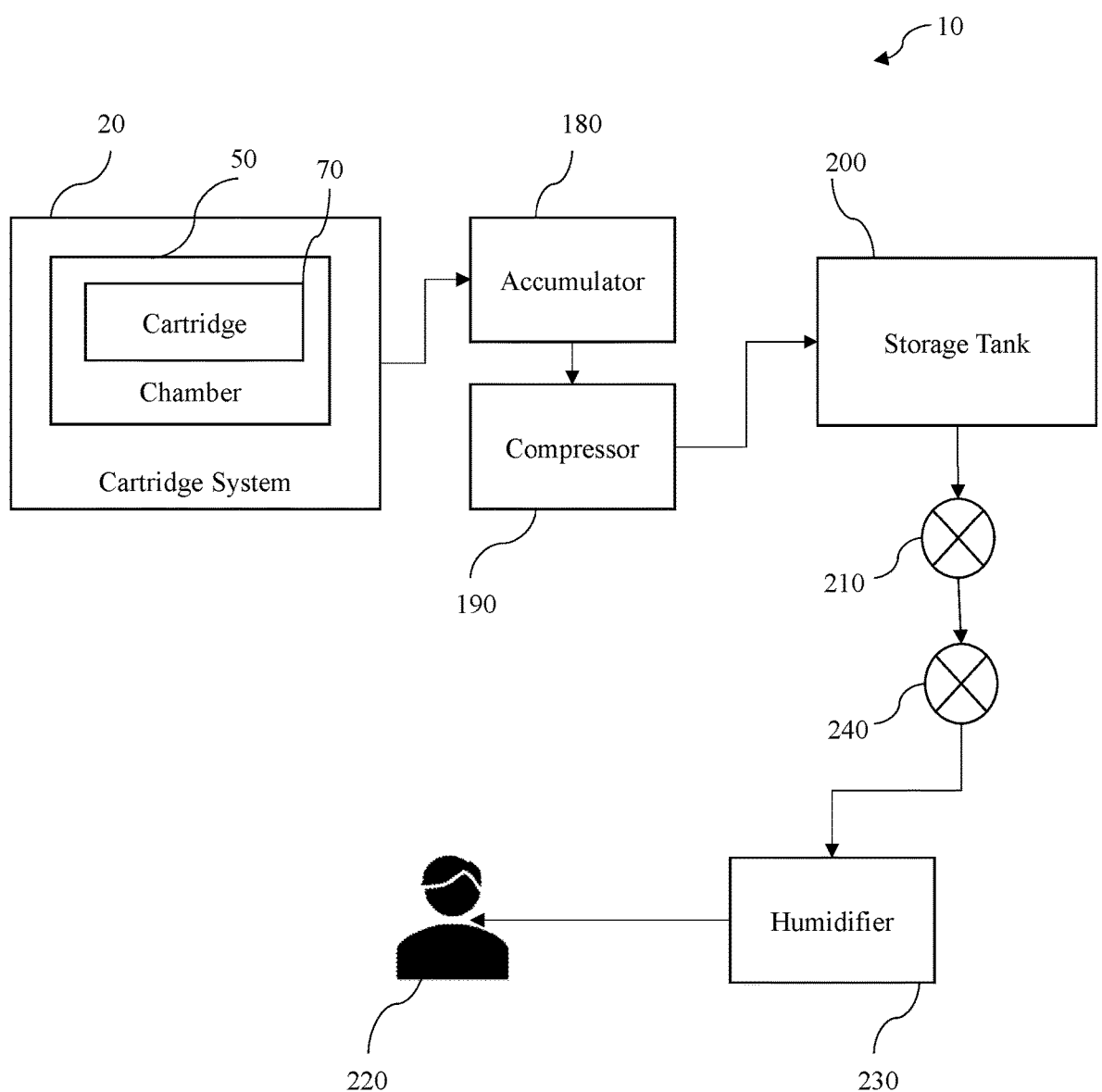
FIG. 2 is a block diagram representation of an embodiment the portable oxygen generator system of FIG. 1 in accordance with an embodiment of the present disclosure.
Figure 3:
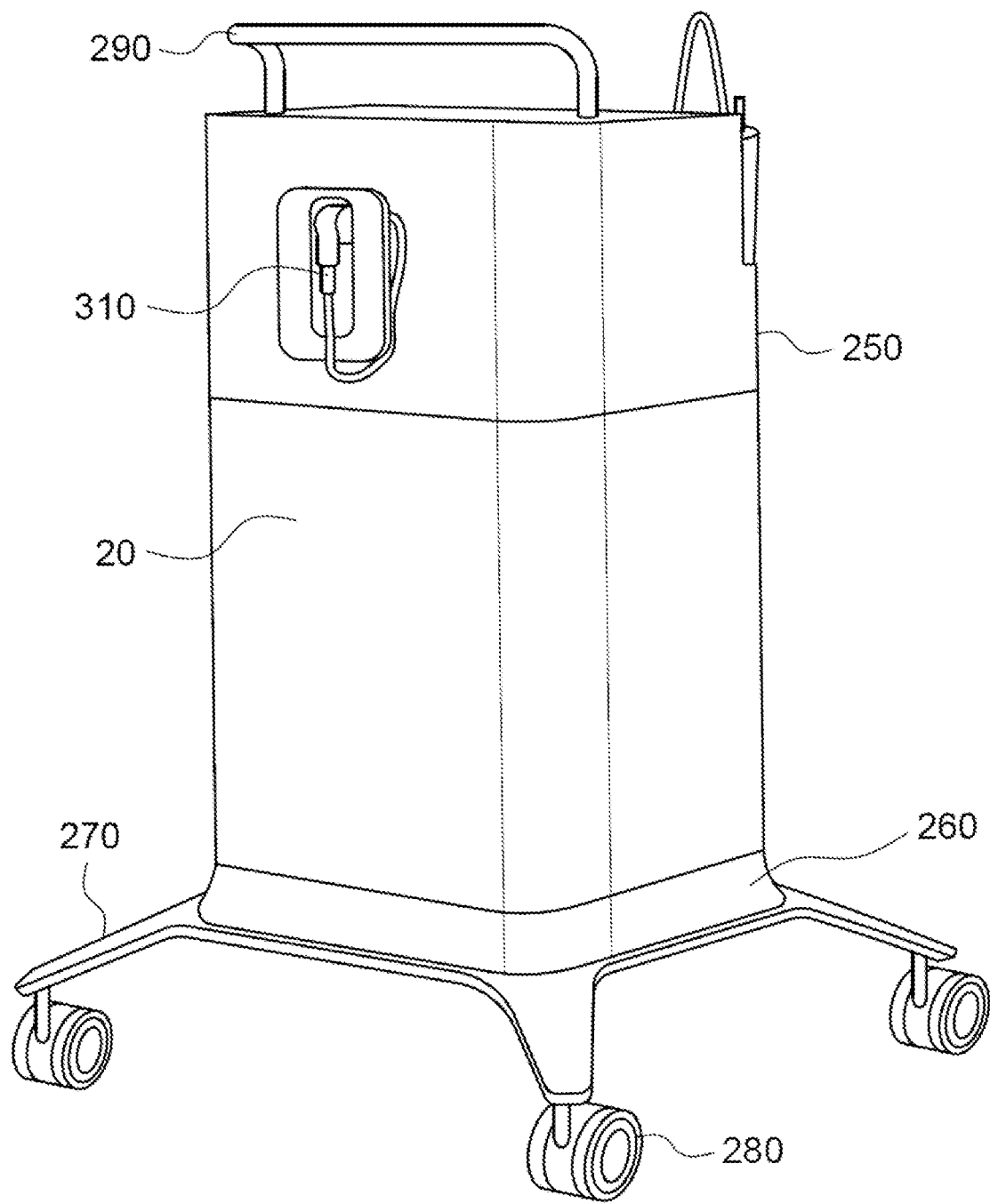
FIG. 3 is a schematic representation of another embodiment representing a cartridge system sealed below a pneumatic circuitry of the portable oxygen generator system of FIG. 1 in accordance with an embodiment of the present disclosure.
Figure 4:
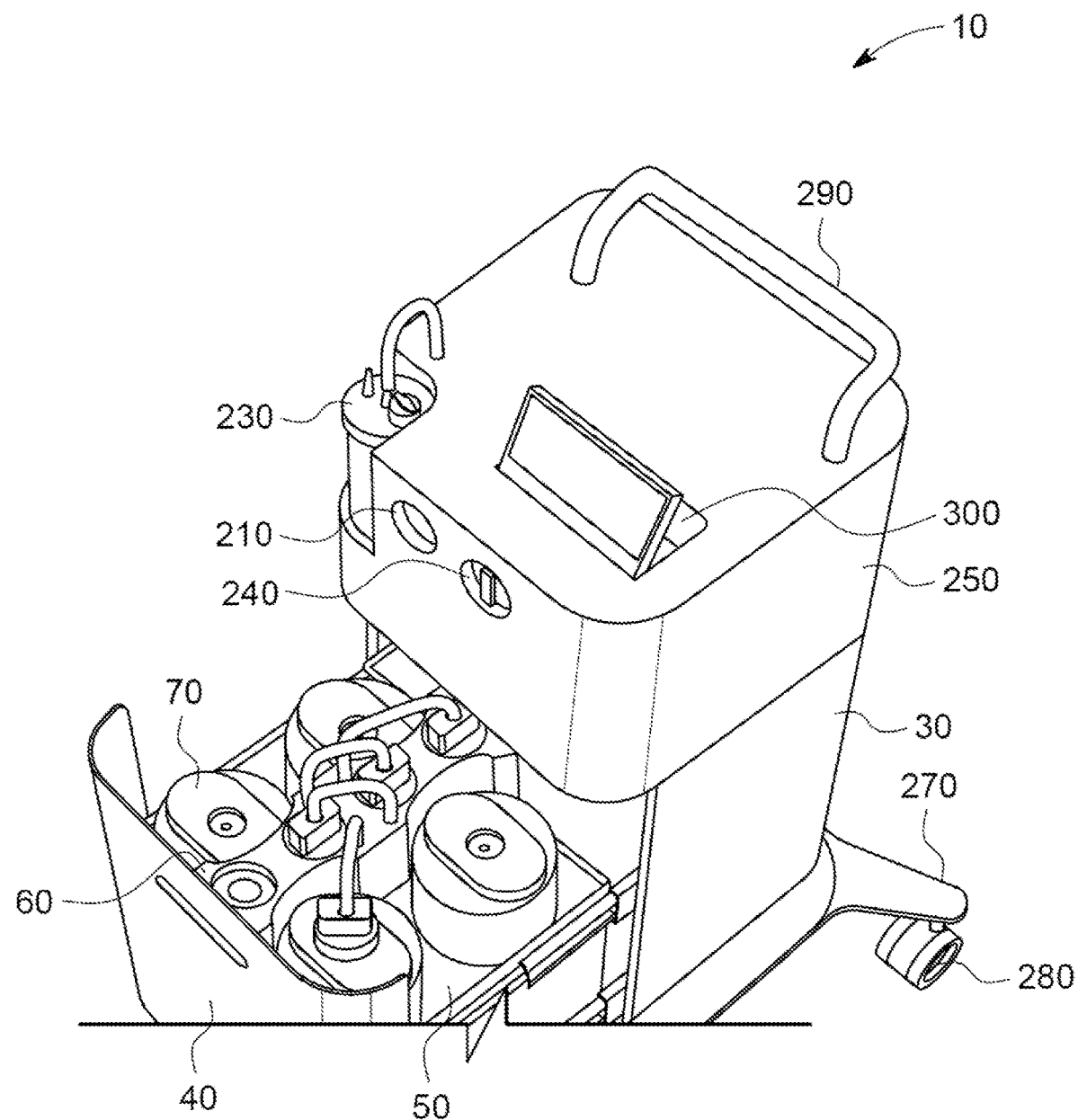
FIG. 4 is a schematic representation of yet another embodiment representing the cartridge system sealed below the pneumatic circuitry of the portable oxygen generator system of FIG. 1 representing a generator draw being open in accordance with an embodiment of the present disclosure.

Turning to FIGS. 1 to 4, FIG. 1 is a schematic representation of a portable oxygen generator system in accordance with an embodiment of the present disclosure. FIG. 2 is a block diagram representation of an embodiment the portable oxygen generator system of FIG. 1 in accordance with an embodiment of the present disclosure. FIG. 3 is a schematic representation of another embodiment the portable oxygen generator system of FIG. 1 in accordance with an embodiment of the present disclosure. FIG. 4 is a schematic representation of yet embodiment the portable oxygen generator system of FIG. 1 representing a generator draw being open in accordance with an embodiment of the present disclosure.

The portable oxygen generator system 10 includes a cartridge system 20 having a container 30 having a generator drawer 40 operable in a lateral direction. In one embodiment, the container 3 may be a rectangular container extended vertically. As used herein, the term "drawer" is defined as a box-shaped container that fits into a piece of furniture in such a way that it can be drawn out horizontally to reach its contents. In one embodiment, operation of the generator drawer 40 may correspond to one of opening or closing the generator drawer 40 via an operable means in a horizontal direction with respect to a ground surface.

The generator drawer 40 includes at least four hollow chambers 50 which are separated by a pre-defined structure 60. In one embodiment, the pre-defined structure 60 may be a partition dividing the generator drawer 40 into two halves. Each of the two halves is configured to have at least two of the at least four hollow chambers 50. The pre-defined structure 60 may be composed of a solid material.

The cartridge system 20 also includes at least four cartridges 70 housed within the corresponding at least four hollow chambers 50. The at least four cartridges 70 are configured to generate oxygen upon reaction of a pre-defined amount of water with one or more chemicals in a chemical chamber 90 located within the at least four cartridges 70. As used herein, the term "cartridge" is defined as a hollow container for holding material used for an insertion into a mechanism. The operation of the generator drawer 40 enables a user to insert and detach the at least four cartridges 70 from the corresponding at least four hollow chambers 50. In one exemplary embodiment, each of the at least four cartridges 70 may be coupled with a handle which is configured to operate the at least four cartridges 70. In such embodiment, operation of the at least four cartridges 70 may include loading and unloading the at least four cartridges 70 into the corresponding at least four hollow chambers 50.

Figure 7:
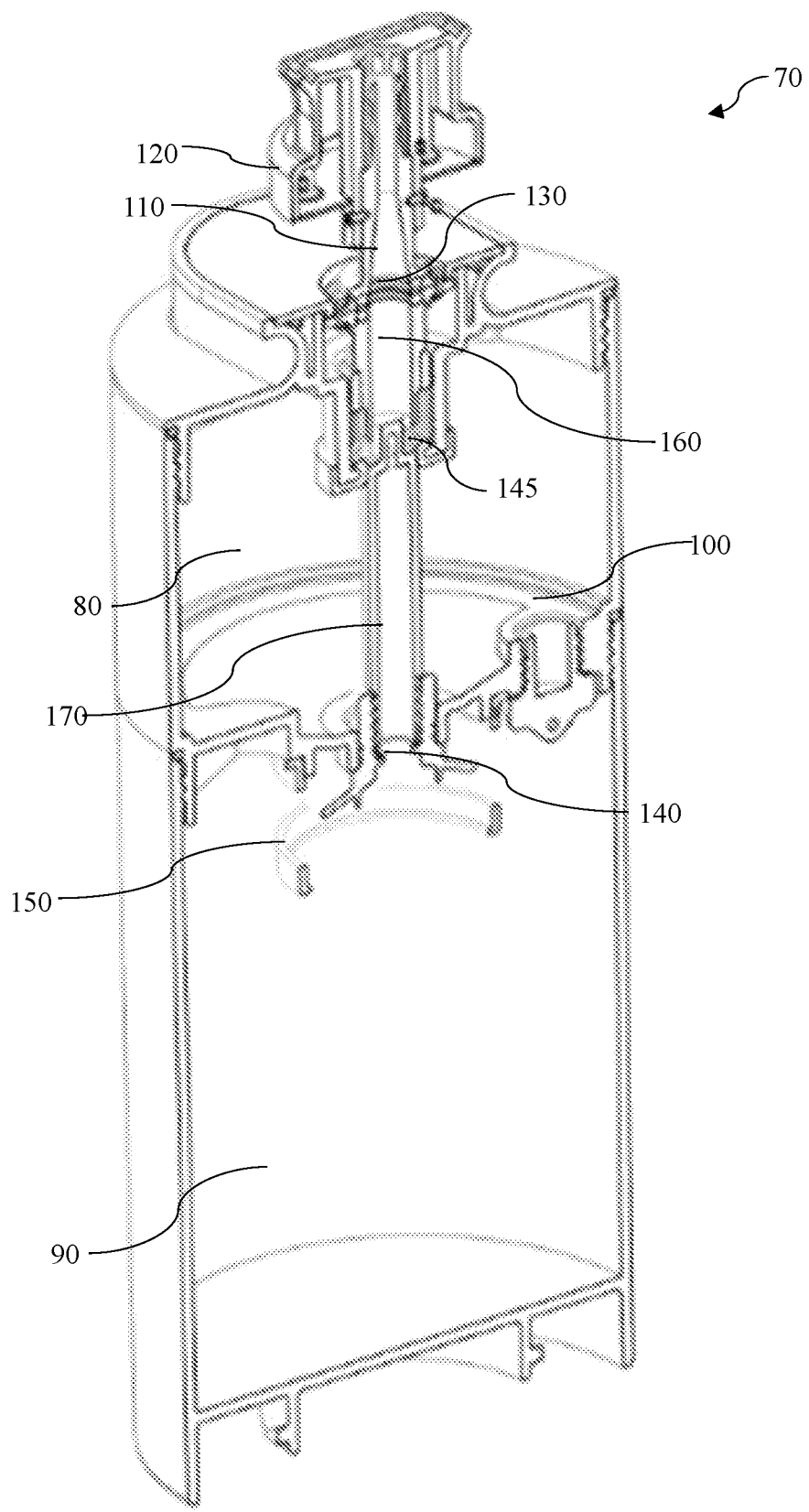
FIG. 7 is a schematic cross-sectional view of a cartridge of the portable oxygen generator system of FIG. 1 in accordance with an embodiment of the present disclosure.

In one exemplary embodiment turning to FIG. 7, each of the at least four cartridges 70 include a water chamber 80 configured to store the pre-defined amount of water. The cartridge 70 also includes a chemical chamber 90 mechanically coupled to the water chamber 80 which is configured to store one or more chemicals in a pre-defined ratio. The water chamber 80 is placed above the chemical chamber 90 and is separated by a disc 100 and is pneumatically sealed.

In one exemplary embodiment, the one or more chemicals may include at least one of sodium percarbonate, potassium superoxide, peroxide species hydrogen peroxide, urea-hydrogen peroxide and percarbamide peroxide. In one specific embodiment, the chemical chamber 90 of each of the at least four cartridges 70 may include a mechanical stirrer configured to keep the one or more chemicals in the chemical chamber 90 in constant mixing.

Further, the cartridge 70 includes a holding means 110 mechanically coupled to an interior top portion of the corresponding at least four cartridges 70. The cartridge 70 also includes a triggering means 120 configured to activate the the at least four cartridges 70. In an embodiment, the system is configured to trigger all the four cartridges simultaneously by activating the corresponding triggering means 120. In another embodiment, the system is configured to trigger one or more cartridges in sequential manner by activating the corresponding triggering means 120. In such an embodiment, the sequential triggering may be regulated by setting a pre-defined gap of time for triggering a next cartridge. The gap of time may be equivalent or less than a duration for which one cartridge is capable of generating oxygen. Further, the sequential triggering may also be regulated based on detection of decline in one of air pressure or gas pressure. In one embodiment, the pressure in the corresponding at least four cartridges 70 may be detected using one or more pressure sensors.

In one exemplary embodiment, the triggering may be done manually. In another exemplary embodiment, a controlling means may be equipped and communicatively coupled to each of the at least four cartridges 70. The controlling means may be configured to trigger the at least four cartridges 70 either all at a time, one by one in a sequential manner or at least two at a time. In such embodiment, the one or more pressure sensors may be communicatively coupled to the controlling means, wherein the controlling means may generate a trigger notification based on sensed pressure by the one or more pressure sensors. Further, a motor may be electrically coupled to the triggering means 120 to activate the triggering means 120 automatically using one of the pre-defined gap of time, the pressure within each of the at least four cartridges 70, oxygen level in the at least one storage tank 200, quantity of oxygen required for the patient 220, or a combination thereof. In one embodiment, the triggering means 120 may be enable with a push feature, wherein the activation of the triggering means 120 may be done by pushing a top seal 130 and hence a trigger valve 160 of the triggering means 120. In one exemplary embodiment, the storage tank 200 may be held outside the portable oxygen generator system 10 and may be operatively coupled to the at least four cartridges 70 for storing the generated oxygen. In such embodiment, the storage tank 200 may be independent of the portable oxygen generator system 10.

Further, the cartridge 70 includes a holding means 110 mechanically coupled to an interior top portion of the corresponding at least four cartridges 70. The cartridge 70 also includes a triggering means 120 configured to activate the at least four cartridges 70. The triggering means 120 is mechanically held in place by the holding means 110. The triggering means 120 includes the top seal 130 configured to unlock a bottom seal 140 upon twisting a trigger connector 145 to a pre-defined angle. As used herein, the term "triggering means" is defined as a means used to trigger or cause a particular reaction based on a particular action. In one embodiment, the trigger connector 145 is placed on a top surface of the pre-defined structure which is configured to keep the connection of the at least four cartridges 70 in place during the generation of oxygen.

The triggering means 120 also includes a trigger valve 160 operatively coupled to the top seal 130 which is configured to enable a process of generation of oxygen. The triggering means 120 further includes a hollow seal tube 170 located along a central axis of the corresponding at least four cartridges 70. As used herein, the term "central axis" is defined as an imaginary straight line passing vertically about a centre of an object.

The triggering means 120 also includes the bottom seal 140 operatively coupled at a bottom of the hollow seal tube 170. The bottom seal 140 is configured to allow the pre-defined amount of water to enter the chemical chamber 90 via a filter 150. The filter 150 is fixed to the disc within the chemical chamber 90. The hollow seal tube 170 is configured to allow flow of oxygen generated from chemical chamber 90 to the water chamber 80. The hollow seal tube 170 is also configured to allow flow of oxygen generated in the chemical chamber 90 upon reaction of the pre-defined amount of water with the one or more chemicals to exit from the water chamber 80. In one specific embodiment, the cartridge system 20 may include two triggering means 120, wherein each of the triggering means 120 may be configured to trigger at least two of the at least four cartridges 70 at a time.

Furthermore, the portable oxygen generator system 10 includes a compressor 190 operatively coupled to the accumulator 180. The compressor 190 is configured to receive accumulated oxygen from the accumulator 180 and compress received oxygen, thereby reduces volume required to store the compressed oxygen. In one embodiment, the compressor 190 may be an oil free compressor configured to compress oxygen from the accumulator 180.

The portable oxygen generator system 10 also includes the at least one storage tank 200 operatively coupled to the compressor 190. The at least one storage tank 200 is configured to store the compressed oxygen received from the compressor 190. In one exemplary embodiment, the compressed oxygen from the accumulator 180 may be transmitted to the at least one storage tank. In one specific embodiment, capacity of the storage of the at least one storage tank 200 may correspond to about 500 litres of the compressed oxygen.

Furthermore, the portable oxygen generator 10 also includes a humidifier means 230 operatively coupled to the at least one storage tank 200. The humidifier means 230 is configured to impart humidity to the oxygen being released from the at least one storage tank 200 to the output coupled to the patient 220 to supply the oxygen. As used herein, the term "humidity" is defined as amount of water vapour present in air. In one exemplary embodiment, the humidifier means 230 includes a container to store water which may be used to humidify the generated oxygen.

In one exemplary embodiment, the humidifier means 230 may also include an inlet valve operatively coupled to a top surface of the humidifier. The inlet valve may be configured to allow the flow of generated oxygen from the at least four cartridges to the accumulator. The humidifier means 230 also includes an outlet valve operatively coupled to the top surface of the humidifier means 230. The outlet valve may be configured to allow the flow of humidified oxygen generated in the at least one storage tank 200.

The portable oxygen generator system 10 also includes an oxygen pressure regulator 210 operatively the at least one storage tank 200. The oxygen pressure regulator 210 is configured to enable a uniform flow of oxygen at pre-defined oxygen pressured required for breathing at an output coupled to a patient 220 to supply the oxygen upon being humidified. The portable oxygen generator system 10 also includes an oxygen flow control knob 240 operatively coupled to the oxygen pressure regulator 210 and the at least one storage tank 200. The oxygen flow control knob 240 is configured to regulate flow ratio of the oxygen being supplied to the patient 220 in an instant.

Figure 5:
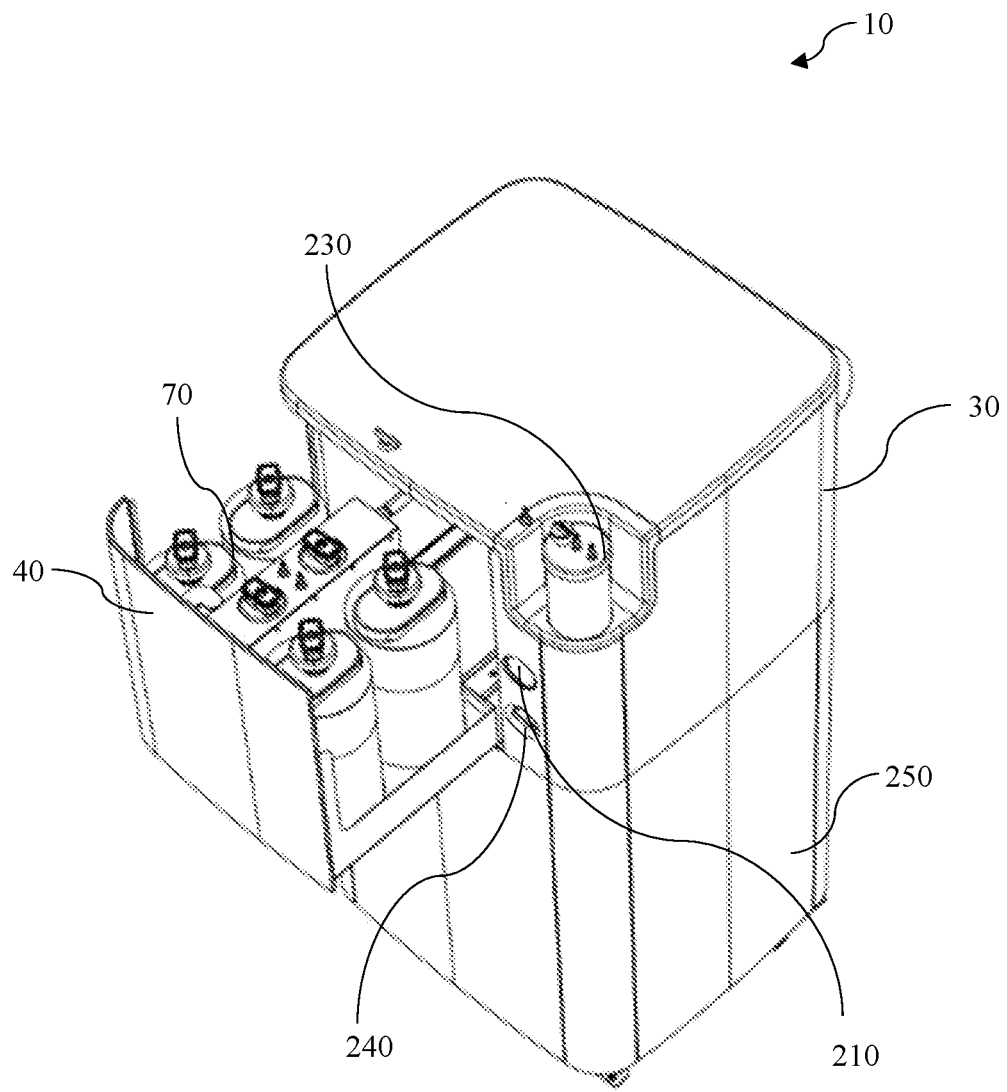
FIG. 5 is a schematic representation of yet another embodiment representing the cartridge system sealed above the pneumatic circuitry of the portable oxygen generator system of FIG. 1 representing a generator draw being open in accordance with an embodiment of the present disclosure.
Figure 6:
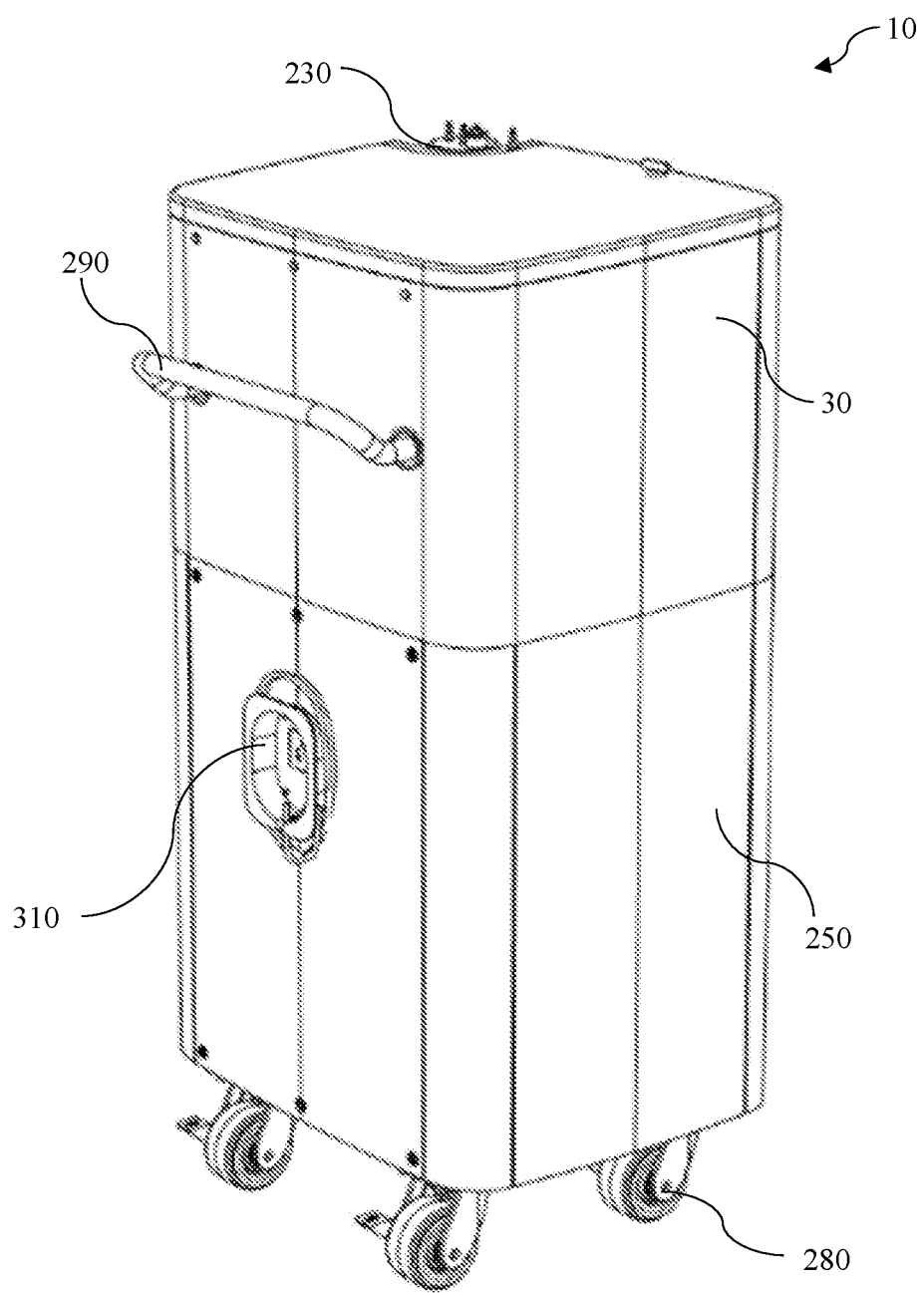
FIG. 6 is a schematic representation of yet another embodiment representing the cartridge system sealed above the pneumatic circuitry of the portable oxygen generator system of FIG. 5 representing a generator draw being open in accordance with an embodiment of the present disclosure.

Furthermore, the portable oxygen generator system 10 also includes a pneumatic circuitry means 250 sealed to the cartridge system 20. In one exemplary embodiment, the pneumatic circuitry means 250 may be sealed above the cartridge system 20. In another exemplary embodiment, the pneumatic circuitry means 250 may be sealed below the cartridge system 20 (as shown in FIG. 5 and FIG. 6.)

The pneumatic circuitry means 250 includes an electronic control circuit configured to control an operation of the compressor 190. The humidifier means 230 is housed on one of a corner of the pneumatic circuitry means 250 which may allow the view of the level of water in the container of the humidifier means 230. Also, the oxygen flow control knob 240 is attached to a body of the pneumatic circuitry means 250 which enables the user to adjust the flow as required. In one exemplary embodiment, the pneumatic circuitry means 250 may include a rechargeable battery unit which may be configured to recharge the one or more batteries housed within the portable oxygen generator 10.

In one exemplary embodiment, the portable oxygen generator 10 may further include a cooling mechanism operatively coupled to each of the at least four cartridges 70. The cooling mechanism is configured to dissipate heat from each of the at least four cartridges 70.

The portable oxygen generator system 10 also includes a wheelbase 260 attached to a bottom surface of one of the cartridge system 20 or pneumatic circuitry means 250 to impart mobility of the portable oxygen generator system 10. In one embodiment, multiple corners of the wheelbase 260 includes a plurality of extensions 270 in corresponding plurality of directions. Each of the plurality of extensions 270. The one or more wheels 280 are affixed to bottom of each of the plurality of extensions 270. The portable oxygen generator system 10 is configured to facilitate unidirectional flow of oxygen generated in the at least four cartridges 70 via a plurality of valves to the humidifier means 230. In one exemplary embodiment the plurality of extensions 270 may be four extensions, each of the four extensions in each corner of the cartridge system 20. In such embodiment, the plurality of wheels 280 may be four wheels, each of the four-wheel placed on each of the corresponding four extensions 270. In one exemplary embodiment, the one or more wheels 280 may be coupled to one of the generator drawer 40 or the pneumatic circuitry means 250 using a coupling means such a screw, bold, or the like (as shown in FIG. 5 and FIG. 6).

Furthermore, in one embodiment the portable oxygen generator system 10 includes a handle 290 mechanically coupled to a top surface of the pneumatic circuitry means 250. The handle 290 is configured to enable the user to port the oxygen generator 10 within a pre-defined environment via the plurality of wheels 280.

In one specific embodiment, the portable oxygen generator system 10 may further include a power cord 310 operatively coupled to one side of the pneumatic circuitry means 250. The power cord 310 is configured to supply control one of operation of a compressor 190 and a battery unit.

In another specific embodiment, the portable oxygen generator system 10 may further include a display means 300 configured to display a set of information associated with at least one of number cartridges 70 activated in an instant, number of cartridges 70 spent, alert for triggering of next one or more cartridges 70, alert for replacing the spent cartridges 70, the flow ratio of the oxygen being supplied to the patient 220 in an instant, and estimated duration of the release of oxygen. The display means may be housed on the top surface of the pneumatic circuitry means 250. In such an embodiment, the display unit may be digital or analog display screen, a computing device such as a mobile phone, a tablet or the like. The computing device such as a mobile phone, a tablet may be communicatively coupled to the portable oxygen generator system 10 via a wireless or wired network. The wireless network may be established using wireless communication technology such as Bluetooth®, Wi-Fi®, LoRa WAN™, Cellular data, Zigbee®, Bluetooth Low Energy™ (Bluetooth LE or BLE), and the like. The communication via the wireless network enables the users to monitor status of various parameters of the portable oxygen generator system 10, and also regulate or change the parameters from a distant location, if required. For example, if the caregiver notices that the present set of activated/triggered cartridges are about to get over, then the user may trigger the other one or more cartridges to maintain the continuous from a distant location.

The portable oxygen generator system 10 may be IoT enabled.

In one exemplary embodiment, the portable oxygen generator system 10 may further include a plurality of valves which may correspond to standard pipping tubes and fitting connecting the at least four chambers 50, the accumulator 180, the compressor 190, the at least one storage tank 200.

Figure 8:
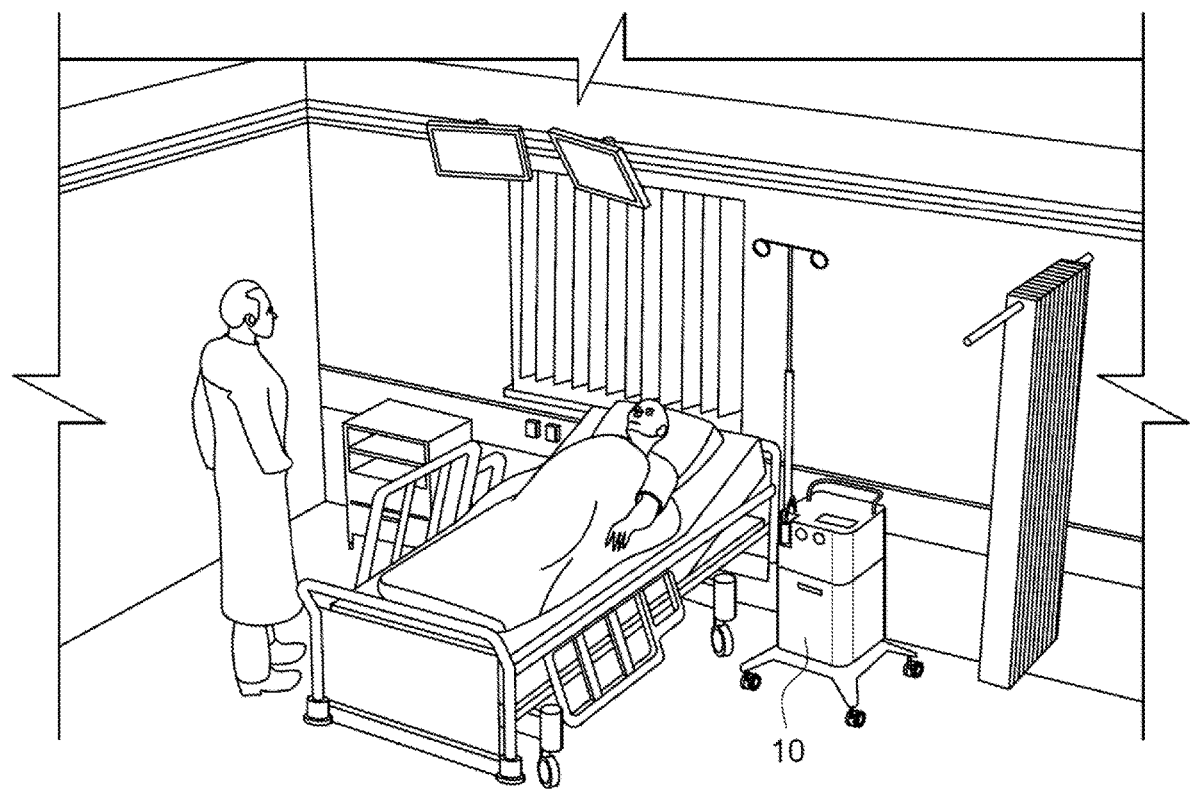
FIG. 8 is a schematic representation of an exemplary embodiment of the portable oxygen generator system being placed in a hospital of FIG. 1 in accordance with an embodiment of the present disclosure.

In operation, turning to FIG. 8 which is a schematic representation of an exemplary embodiment of the portable oxygen generator system being placed in a hospital of FIG. 1 in accordance with an embodiment of the present disclosure. The portable oxygen generator system 10 is ported from one location to another by the user within the hospital by operating the portable oxygen generator system 10 via the plurality of wheels 280 using the handle 290. Further, upon setting the portable oxygen generator system 10 in a required location, the user triggers the triggering connector 145 of the triggering means 120 of a first cartridge of the at least four cartridges 70 by manually twisting to 90 degrees, consequently the top seal 130 and hence the trigger valve 160 of the triggering means 120 of the first cartridge is opened to allow the flow of pre-defined amount of water from the water chamber 80 to enter the chemical chamber 90 via the filter 150 which is controlled by the bottom seal 140. Further, as the pre-defined amount of water is mixed with the one or more chemicals, oxygen is released as a product. Further, the oxygen generated in the chemical chamber 90 is transferred to the outlet via the hollow seal tube 170 passing through the water chamber 80. The oxygen generated in the chemical chamber 90 is then transferred to the humidifier means 230 to impart humidity to the generated oxygen. Also, the level of oxygen left in the first cartridge is indicated by the oxygen level indicator. Furthermore, as the oxygen generated in the first cartridge gets ceased, the triggering connector 145 of the triggering means 120 of a second cartridge of the at least four cartridges 70 is manually twisted to 90 degrees, and the process of generation of oxygen is repeated in the second cartridge as in the first cartridge. The process continues for all the at least four cartridges 70 to generate oxygen continuously.

Various embodiments of the portable oxygen generator system to be portable as it is composed of lighter material and is compact which makes the oxygen generator more reliable. Also, as the cartridges are small and compact, replacement of the cartridges are simple and quick. In addition, as the oxygen generator includes at least four cartridges, flow of oxygen is continuous, and every alternative cartridge can be easily replaced which keeps the flow of oxygen continuous.

Furthermore, the portable oxygen generator system includes the oxygen flow control knob which gives an option for the user to choose the level or rate of oxygen required which makes the oxygen generator is more efficient. Also, due to the plurality of wheels and the handle attached to the portable oxygen generator system, it becomes easy for the user to transport the oxygen generator easily from one location to another.

Also, upon triggering the top seal, the pre-defined amount of water and the one or more chemicals gets combined automatically and reacts accordingly to generate the oxygen which saves time of the user to manually combine the one or more chemicals and the pre-defined amount of water for the generation of oxygen. Due to such non-intervention of human, accuracy on the ratio of the one or more chemicals and the pre-defined amount of water is maintained thereby making the oxygen generator more accurate.

In addition, due to the varied types of triggering means being used in the system, the amount of oxygen to be generated in a given situation can be managed very precisely. Such as more than one patient require oxygen at the same time and there are not enough oxygen cylinders, then more than one cartridge can be triggered and supply oxygen to more than one patient at a time simultaneously. Also, due to the design of the generator draw, the replacement of the cartridges with the cartridge system is easy and is user friendly, which also saves time in replacement of the same in any circumstances. In addition, as the oxygen storage tank is being eliminated from the system, the overall size of the system is being reduced and thereby making the system compact. Also, due to the optional connectivity of the oxygen storage tank outside the generator, the system enables an option for the users to generate and fill the oxygen storage tank as per the requirement.

While specific language has been used to describe the disclosure, any limitations arising on account of the same are not intended. As would be apparent to a person skilled in the art, various working modifications may be made to the method in order to implement the inventive concept as taught herein.

The figures and the foregoing description give examples of embodiments. Those skilled in the art will appreciate that one or more of the described elements may well be combined into a single functional element. Alternatively, certain elements may be split into multiple functional elements. Elements from one embodiment may be added to another embodiment. For example, order of processes described herein may be changed and are not limited to the manner described herein. Moreover, the actions of any flow diagram need not be implemented in the order shown; nor do all of the acts need to be necessarily performed. Also, those acts that are not dependent on other acts may be performed in parallel with the other acts. The scope of embodiments is by no means limited by these specific examples.

I claim:

1. A portable oxygen generator system comprising:
    a cartridge system comprising:
        a container comprising a generator drawer operable in a lateral direction, wherein the generator drawer comprises at least four hollow chambers, wherein the at least four hollow chambers are separated by a pre-defined structure;
        at least four cartridges housed within the corresponding at least four hollow chambers, wherein each of the at least four cartridges is configured to generate oxygen upon triggering a reaction of a pre-defined amount of water with one or more chemicals in a chemical chamber located within each of the at least four cartridges;
    an accumulator operatively coupled to the at least four cartridges via a set of pipes and configured to receive and accumulate the generated oxygen;
    a compressor operatively coupled to the accumulator, and configured to receive accumulated oxygen from the accumulator and compress received oxygen, thereby reduces space required to store the compressed oxygen;
    at least one storage tank operatively coupled to the compressor, and configured to store the compressed oxygen received from the compressor;
    an oxygen pressure regulator operatively coupled to the at least one storage tank, and configured to enable a uniform flow of oxygen at pre-defined oxygen pressure required for breathing at an output coupled to a patient to supply the oxygen from the at least one storage tank;
    an oxygen flow control knob operatively coupled to the oxygen pressure regulator and the at least one storage tank, and configured to regulate flow ratio of the oxygen being supplied to the patient in an instant;
    a humidifier means operatively coupled to the at least one storage tank, and configured to impart humidity to the oxygen being released from the at least one storage tank to the output coupled to the patient to supply the oxygen;
    a pneumatic circuitry means sealed to the cartridge system, wherein the pneumatic circuitry means comprises an electronic control circuit configured to control an operation of the compressor;
    a wheelbase attached to a bottom surface of one of the generator drawer or the pneumatic circuitry means to impart mobility of the portable oxygen generator system; and
    wherein the portable oxygen generator system is configured to facilitate unidirectional flow of oxygen generated in the at least four cartridges via a plurality of valves to the humidifier means.

2. The portable oxygen generator system as claimed in claim 1, wherein the generator drawer being operable in the lateral direction corresponds to one of opening or closing the generator drawer via an operable means in a horizontal direction with respect to a ground surface, where the operation of the generator drawer enables a user to insert and replace the at least four cartridges from the corresponding at least four hollow chambers.

3. The portable oxygen generator system as claimed in claim 1, wherein the cartridge system being housed at one of a bottom and top section of the portable oxygen generator system.

4. The portable oxygen generator system as claimed in claim 1, wherein each of the at least four cartridges comprises:
    a water chamber configured to store the pre-defined amount of water;

a chemical chamber mechanically coupled to the water chamber, and configured to store one or more chemicals in a pre-defined ratio, wherein the water chamber is placed above the chemical chamber and is separated by a disc and is pneumatically sealed;

a holding means mechanically coupled to an interior top portion of the corresponding at least four cartridges;

a triggering means mechanically held in place by the holding means, wherein the triggering means comprises:

a top seal configured to unlock a bottom seal upon twisting a trigger connector to a pre-defined angle;

a trigger valve operatively coupled to the top seal, and configured to enable a process of generation of oxygen;

a hollow seal tube located along a central axis of the corresponding at least four cartridges; and the bottom seal operatively coupled at a bottom of the hollow seal tube, and configured to allow the pre-defined amount of water to enter the chemical chamber via a filter, wherein the filter is fixed to the disc within the chemical chamber, wherein the hollow seal tube is configured to:

allow flow of oxygen generated from chemical chamber to the water chamber; and allow flow of oxygen generated in the chemical chamber upon reaction of the pre-defined amount of water with the one or more chemicals to exit from the water chamber.

5. The portable oxygen generator system as claimed in claim 4, wherein the chemical chamber of each of the at least four cartridges comprises a mechanical stirrer configured to keep the one or more chemicals in the chemical chamber 90 in constant mixing.

6. The portable oxygen generator system as claimed in claim 4, wherein the trigger connector is placed on a top surface of the pre-defined structure, and is configured to keep the connection of the at least four cartridges in place during the generation of oxygen.

7. The portable oxygen generator system as claimed in claim 4, wherein the bottom seal of the triggering means of each of the at least four cartridges is unlocked simultaneously.

8. The portable oxygen generator system as claimed in claim 4, wherein one or more of the at least four cartridges is unlocked sequentially upon unlocking the corresponding bottom seal of the triggering means of the at least four cartridges in a sequential manner.

9. The portable oxygen generator system as claimed in claim 8, wherein the unlocking of the at least four cartridges is activated by one of setting a pre-defined gap of time for triggering a next cartridge, detection of decline in one of air pressure or gas pressure within one or more of the triggered cartridges, oxygen level in the at least one storage tank, quantity of oxygen required for the patient, or a combination thereof.

10. The portable oxygen generator system as claimed in claim 1, wherein the at least one storage tank is housed within the cartridge system.

11. The portable oxygen generator system as claimed in claim 1, wherein the one or more chemicals comprises at least one of sodium percarbonate, potassium superoxide, peroxide species (hydrogen peroxide), urea-hydrogen peroxide and percarbamide peroxide.

12. The portable oxygen generator system as claimed in claim 1, further comprises a cooling mechanism operatively coupled to each of the at least four cartridges, and configured to dissipate heat generated from each of the at least four cartridges during generation of the oxygen.

13. The portable oxygen generator system as claimed in claim 1, further comprises a display means communicatively coupled to portable oxygen generator system and configured to display a set of information associated with at least one of number cartridges activated in an instant, number of cartridges spent, alert for triggering of next one or more cartridges, alert for replacing the spent cartridges, the flow ratio of the oxygen being supplied to the patient in an instant, and estimated duration of the release of oxygen.

14. The portable oxygen generator system as claimed in claim 1, further comprises a power cord operatively coupled to one side of the pneumatic circuitry means, and configured to control one of operation of the compressor and a battery unit.

15. The portable oxygen generator system as claimed in claim 1, further comprises a handle mechanically coupled to a side on top of the pneumatic circuitry means, and configured to enable the user to port the oxygen generator system from one location to another.

16. The portable oxygen generator system as claimed in claim 13, wherein the display unit comprises at least one of digital display screen, a computing device, a smart phone, a tablet or combination thereof.

17. The portable oxygen generator system as claimed in claim 13, wherein the display unit being communicatively coupled to the portable oxygen generator system via a wireless communication technology.

* * * * *